United States Patent [19]

Avitall

[11] Patent Number: 5,702,438
[45] Date of Patent: Dec. 30, 1997

US005702438A

[54] EXPANDABLE RECORDING AND ABLATION CATHETER SYSTEM

[76] Inventor: Boaz Avitall, 4868 N. Ardmore Ave., Milwaukee, Wis. 53217

[21] Appl. No.: 482,675

[22] Filed: Jun. 8, 1995

[51] Int. Cl.$^6$ ................................................. A61N 1/00
[52] U.S. Cl. ........................ 607/122; 607/128; 128/642
[58] Field of Search .............................. 607/120–126, 607/128; 128/642; 606/46, 41

[56] References Cited

U.S. PATENT DOCUMENTS

| | | |
|---|---|---|
| 4,522,212 | 6/1985 | Gelinas et al. . |
| 4,699,147 | 10/1987 | Chilson et al. . |
| 5,078,717 | 1/1992 | Parins et al. . |
| 5,117,828 | 6/1992 | Metzger et al. . |
| 5,228,442 | 7/1993 | Imran . |
| 5,255,679 | 10/1993 | Imran ................................... 607/122 |
| 5,263,493 | 11/1993 | Avitall . |
| 5,313,943 | 5/1994 | House ..................................... 606/41 |
| 5,345,936 | 9/1994 | Pomeranz et al. ..................... 128/642 |
| 5,397,342 | 3/1995 | Heil, Jr. et al. ......................... 607/129 |

FOREIGN PATENT DOCUMENTS

| | | | |
|---|---|---|---|
| 246004 | 11/1996 | Russian Federation | 607/128 |
| 9316634 | 9/1993 | WIPO | 128/642 |

*Primary Examiner*—John P. Lacyk
*Attorney, Agent, or Firm*—Haugen and Nikolai, P.A.

[57] ABSTRACT

A recording/ablation system includes an inner working catheter for deployment from a distal port in an outer sheath or catheter in a heart chamber, or the like, which has a plurality of divergent electroded spines each constrained at the proximal end with a substantially free distal end for controlled separation. The divergent electroded spines are collapsible to a substantially parallel configuration for transport and stowage. A single deflecting spine version is also disclosed.

26 Claims, 4 Drawing Sheets

EXPANDABLE RECORDING AND ABLATION CATHETER SYSTEM

BACKGROUND OF THE INVENTION

I. Field of the Invention

The present invention relates generally to the field of recording and ablation using steerable vascular catheters. The invention is particularly directed to an expanding recording and ablation catheter system suitable for the creation of linear continuous lesions for electrical isolation in a vascular chamber, the system being capable of expanding to the size necessary to apply electrodes against the inner surface of a cardiac chamber of interest.

II. Discussion of the Related Art

Steerable vascular catheter systems of several types have been in use for some time. Such devices can be inserted into blood vessels (arteries or veins) and their distal ends navigated through the tortuous path to reach remote areas of interest normally inaccessible except by surgery where procedures are performed. Catheters have been developed of both the steerable or self-navigating type and models threaded over pre-inserted guidewires. Catheters of the class have also been provided for some time with distal electroded sections for monitoring parts of the body, such as for electrically mapping the heart by receiving and transmitting electrical signals related to the operation of that organ to recording signal processing and display devices.

The ability to successfully record impulses or signals and from them electrically map cardiac chambers and valves using flexible catheters having steerable electroded tips has further led to the development of techniques for transcatheter ablation of cardiac tissues that have been identified as the electrical pathways that enable and sustain cardiac arrhythmias. This technique has emerged as one of the most important advances in cardiac electrophysiology. Its goal is to electrically decouple the arrhythmogenic tissue without compromising the mechanical or muscular integrity of the cardiac tissues and vessels.

Not long ago, for example, many patients with Wolff-Parkinson-White syndrome or ventricular tachycardia were forced to undergo surgical dissection of the arrhythmogenic tissue followed by a painful and prolonged recovery. Introduction of the transcatheter approach has dramatically reduced the suffering and cost of definitive treatment to alleviate many cardiac arrhythmias.

The general approach to this procedure initially preferably utilized high energy direct current delivered to the catheter poles, for example, to disrupt the A-V node condition and even to create a complete heart block by ablating the His bundle. More recently, however, radio frequency has replaced high energy direct current as the preferred primary source of energy and the transcatheter approach for cardiac ablation has become an accepted and common procedure and has been used increasingly as the primary mode of treating cardiac arrhythmias. Transcatheter cardiac tissue ablation is more fully discussed in Avitall et al, "Physics and Engineering of Transcatheter Tissue Ablation", JACC, Volume 22, No. 3:921-32. The rapid clinical acceptance of this procedure and the proliferation of physicians engaged in transcatheter tissue ablation has mandated the development of improved steerable catheter devices.

Other common cardiac arrhythmias previously untreatable except with medication, and more recently, surgery, involve atrial fibrillation and flutter. These conditions, in fact, are the most common rhythm disturbances in human beings. Approximately 1% of the population of the United States, i.e., more than 2.5 million people, depends on medication to control this condition. These irregular heart rhythms can reach rates of 180 beats/minute or more. The resulting loss of blood flow due to incomplete atrial contractions along with a rapid heart rate can lead to shortness of breath, dizziness, limited physical endurance, chest pains (in patients with coronary heart disease), and other related problems.

Recently, Dr. Cox et al of Washington University School of Medicine in St. Louis, Mo., have devised a surgical procedure called the Maze and Corridor operation. This procedure is an attempt to restore the normal heart rhythm by segmenting the atrial tissues in a manner that allows the normal heart pacemaker to conduct to the AV node as well as preventing the atrial tissues from sustaining the atrial fibrillation.

It has been demonstrated that surgical incisions placed in the left and right atrium in specific locations to form a maze pattern eliminates longstanding atrial fibrillation in upwards of 80%–90% of patients. By cutting the atrial tissue, electrical barriers are created that partially isolate adjacent regions of atrial wall from electrically communicating with each other so as to limit the atria from sustaining the disorganized electrical activity that represents atrial fibrillation. The approach, while successful, involves a long, difficult surgical procedure that may be associated with bleeding complications as a result of the extensive intervention and has the same additional drawbacks as other previous surgical approaches with respect to the recovery of the patient. This represents another area of cardiac arrhythmic treatment where a more benign approach, i.e., without invasive surgery, would represent a definite advance.

In this regard, it has also been demonstrated that electrical decoupling of tissues by heating the tissues to about 55° C. or higher with radio frequency (RF) energy, microwave energy, laser energy, freezing of the tissue or sonication represent possible alternative approaches that lead to cellular destruction and a later replacement of the destroyed or ablated tissues by connective tissues that are electrically silent effectively decoupling regions from electrically communicating. It has been found that segmenting tissues by creating continuous linear lesions via transcatheter ablation in the atria successfully mimics some aspects of the maze and corridor procedure.

The most important aspect of these lesions is their transmural and continuous character; otherwise, segmenting the heart and preventing fibrillation would not be possible. However, it is possible that limited division of tissues may prevent fibrillation in some patients. Furthermore, segmenting a corridor between the sinus node and the AV node will maintain physiological control of heart rate despite fibrillation in the atrial tissues.

Thus, ablation in selected regions of the human heart muscle that need to be electrically decoupled so as to reduce the size of the muscle mass that can sustain and perpetuate fibrillation is recognized. Radio frequency heating of active tissue results in damage that can render the tissue electrically silent. Creation of linear lesions in this manner in the tissue electrically segments the muscle into small enough regions to eliminate or significantly modify fibrillation.

While theoretically feasible, however, as a practical matter it is difficult to position and maintain placement of an ablation catheter system long enough for successful ablation. Present steerable catheter systems, while successful in addressing many internal cardiac areas, have not been so successful in treating atrial fibrillation, for example, because they have not been able to sustain contact with certain surface areas of the atrial chambers without great difficulty. In addition, such devices carry an ablating electrode only at the distal catheter tip so that only one short lesion can be created at a time and it is very difficult to reposition the electrode to create linear lesions. The procedure is quite tedious and extremely time consuming and is unlikely to be successful. Improvements in mapping and ablation catheter systems that facilitate successful creation of continuous linear lesions in the atria or elsewhere would represent a definite advance in the treatment of this condition.

In order to create RF linear lesions, the electrodes from which the RF energy is delivered must be in good contact with the tissues. Since the cardiac chambers are complex structures, a catheter system which can adapt to the tissues structures and maintains good contact is needed.

Accordingly, it is a primary object of the invention to provide an improved recording/ablation electrode deploying device, easily deployed and maneuvered to establish and sustain electrode contact with inner wall surfaces of the any cardiac chamber where desired so that linear lesions can be produced as required.

Another object of the invention is to provide a method of readily deploying an ablation system and accurately mapping and ablating in a cardiac chamber of interest.

Yet another object is to provide multi-electrode expandable recording/ablation devices that are easily deployed from sheath or catheter lumens once the desired chamber is breached.

An additional object of the invention is to provide controlled, resilient expanding working catheter shapes capable of readily expanding to open the chamber and address and hold electrode location on internal surfaces of varying contour while maintaining linear electrode disposition.

Still another object of the invention is to provide an improved multi-electrode mapping and ablation catheter for deployment in cardiac chamber having spines characterized by a controlled unfolding and folding V or wishbone shape.

Yet still another object of the invention is to provide an improved single-spine, multi-electrode mapping and ablation system for deployment in a chamber that uses a plurality of axially operable connected control elements to control the shape of the electroded spine.

A further object of the invention is to provide an improved multi-electrode expandable mapping and ablation catheter capable of positioning one or more electrodes against opposite cardiac chamber sides with reference to the wall of a chamber.

A still further object of the invention is to provide an expandable multi-electrode mapping or ablation catheter for deployment in a cardiac chamber that opens upon deployment from the distal end of a sheath to a memoried shape.

A yet still further object of the invention is to provide an expandable multi-electrode mapping or ablation catheter for deployment in a cardiac chamber that opens upon deployment from the distal end of a sheath using a control wire system.

Other objects and advantages of the invention will become apparent to those skilled in the art in accordance with the descriptions and Figures of this specification.

SUMMARY OF THE INVENTION

The present invention provides an array of readily controlled recording/ablation electroded spine or spine catheter shapes that are easily deployed and expanded to contact the inner wall surface of a cardiac chamber spanning the chamber and pushing against the endocardial surfaces. This creates good electrical contact for recording or mapping of activity and thereafter sustains stabilized contact so that accurate linear or local lesions can be produced. Embodiments range from those using a pair of electrodes to those using multiple arrays of mapping and ablation electrode devices serially spaced along the working catheter shape using radio frequency ablation energy.

The working electroded spine section is deployed from a main catheter or sheath and may consist of a single spine or multiple, proximally constricted spine members. The single spine version can assume any shape from almost linear to circular and a two-spine version assumes a generally spreading V or wishbone configuration. A multi-spine, three-dimensioned system is also contemplated.

The catheter system of the invention includes a diverging or working electroded spine or spines which may be catheters deployable from a distal opening in an outer vascular catheter or sheath tube of larger diameter designed to be deployed in a cardiac chamber of interest. The outer catheter is first inserted and is caused to navigate the vascular system of the patient in a conventional manner, with or without a guidewire, depending on the model used, to the relevant chamber of the heart or other organ where the procedure is to be performed.

The electroded working spine or catheter system is carried by and attached to or integrally forms the distal portion of an inner member or catheter designed to be inserted into the outer catheter or sheath (once the distal end of the outer catheter or sheath is located where desired), and emerge from the distal end of the sheath to be opened or expanded within the chamber of interest just prior to the procedure. After completion of the procedure, or for catheter exchange, the diverging catheter is readily refolded or collapsed and withdrawn back into the outer catheter or sheath where it can be removed followed by removal of the outer catheter or possibly the insertion of another electroded catheter model. In this manner, exchange of working catheter models as needed during the procedure is also easily accomplished.

One embodiment of the electroded spine system of the invention consists of a pair of dual spines designed to diverge from a common proximal origin to form a generally V or wishbone shape. One or more connecting members span the V at spaced locations and attach intermediately to an axially operating control member that operates to fold or relax the one or more connecting members. Each spine of the V carries a tip ablation electrode and one or more additional ablation or mapping electrodes extending along each spine proximal the distal tip. The V expands based on the relaxed configuration of memoried material such as nitinol® or a spring biased material. The shape is collapsed or folded using an operable control mechanism that controls the width of the V. In this manner, the V portion of the catheter may be designed to be opened and closed utilizing a connecting wire system that forces the spines to spread open or fold as needed.

A two-electrode embodiment has a pair of separated ablation electrodes at the distal tips of the V, nominally 7 or 8 French in diameter and about 4 to 5 mm long in combination with spaced recording ring electrodes which may be 2 mm in length but which may have a length up to that of the ablation electrodes. The system is designed to create one or two oppositely disposed linear lesions in a heart chamber by first establishing an initial contact point on one or both opposing walls of the chamber established as by using the mapping electrodes and ablating the site by selectively energizing one or both ablation electrodes. A single connecting member spans the V in the vicinity of the distal end and is attached midway to an axially operating control member which collapses the system to close or allows it to expand to open. The open system is then moved a short distance along the desired path of a linear lesion (or lesions) and the operation repeated until desired ablation is accomplished. The outward pressure applied by the two electrodes enables the system to maintain contact with the tissue on opposing walls of the chamber which are continuously animated. The sequential repetition after small incremental movement of the system along the wall enables the system to create one or more linear lesions.

Each 2 mm or other size recording ring may be located possibly 2-4 mm proximally to an ablation electrode and allows bipolar recording associated with proper location of ablation sites. However, any convenient size and spacing may be employed that enables successful procedures to be performed in accordance with the invention. The inside facing surfaces of the ablation electrodes are optionally flattened to reduce the diameter of the folded system.

In an alternate embodiment of the invention, the V-shaped system includes multiple ablation electrodes (possibly 4-5 mm long ring electrodes spaced 3-4 mm from each other) along the legs of the V. The wire expansion/contraction system consist of multiple connectors connected between the spines of the V at spaced locations and intermediate the spines to a common axially operating control element or pull wire. This version enables, in certain cases, linear lesions to be created in a single step, i.e., without the necessity of incrementally moving the position of the working catheter and re-energizing the ablation electrodes. Other multiple strand or spine systems expandable to form distally open, three-dimensional shapes are also possible in which, for example, four spine elements are interconnected in intersecting pairs with connector elements and folded or collapsed by a common control element.

As indicated, the spine system of the invention is designed to be used with a previously inserted outer catheter or sheath and the system including the electrical harness and expansion or control wire is carried in an inner member or catheter inserted and passed via the sheath into the chamber of interest. Insertion and withdrawal of the catheter is done by collapsing the catheter with a control wire or other filament and retracting it into the sheath. The axial control member is devised to operate axially to collapse the system either by pulling so that the expansion spines will collapse inward (toward the outer catheter or sheath) or by pushing the spines outward which, of course, requires the control member to be rigid enough to operate the system.

Each electrode is separately connected and each spine carries the corresponding number of connecting conductors internally in a lumen or imbedded in the spine, the electrodes having the ability to be energized in any pattern or connected for receiving (recording) as desired. This allows complete operating flexibility in both recording and ablation.

BRIEF DESCRIPTION OF THE DRAWINGS

In the drawings, wherein like numerals are utilized to designate like parts throughout the same.

DETAILED DESCRIPTION

The expanding catheter of the invention contemplates an elongated member designed to traverse a catheter or sheath lumen and carry at its distal end spines essentially of common or abutting origin that are collapsed to a substantially parallel configuration for transport and diverge resiliently upon relaxation or deployment. The spines carry electrodes for recording and ablation which may be individual electrodes or a number of electrodes serially arranged along the spines. The configuration of the spine can also take any of several forms.

Figure 3:
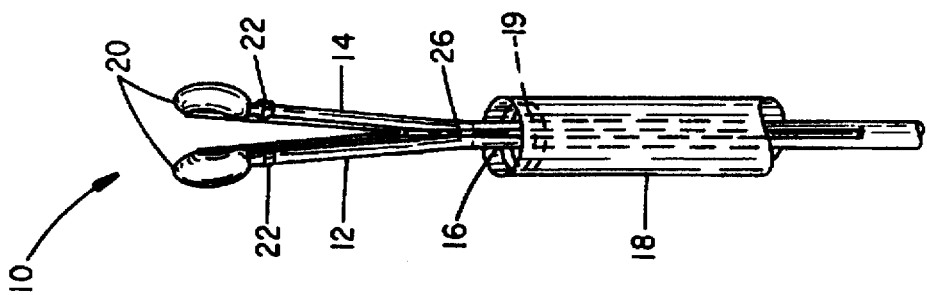
FIGS. 1-3 depict the two-ablation electrode embodiment of the working catheter system of the invention in a fully expanded, partially expanded and collapsed condition, respectively.
Figure 2:
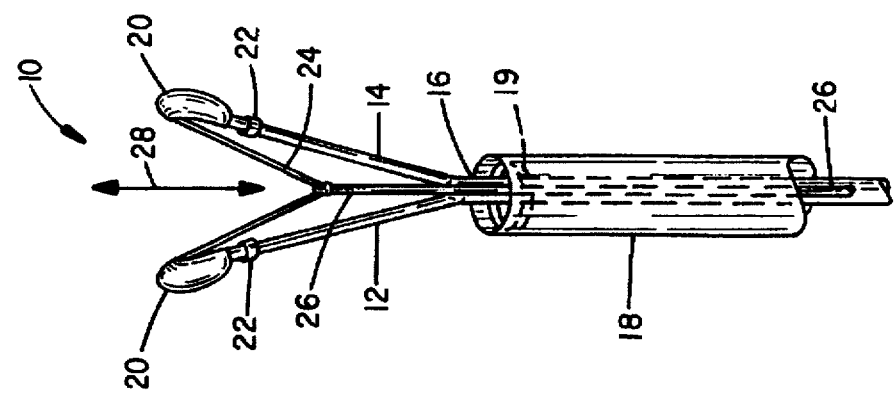
Figure 1:
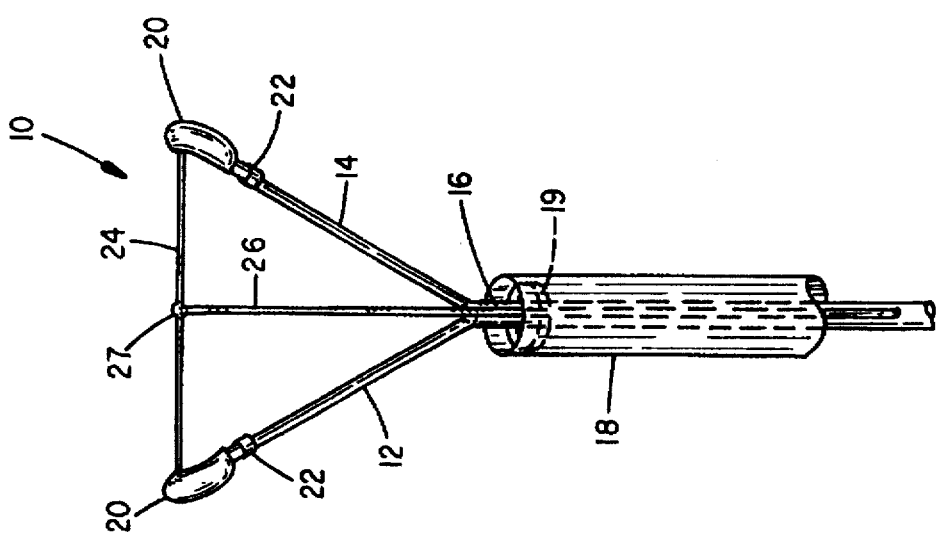

FIGS. 1-3 depict a two-electrode version of the expanding catheter of the invention, generally at 10, at various stages of expansion and/or collapse. FIG. 1 depicts the system as fully extended or expanded and it includes dual diverging spines 12 and 14 which form the distal portion of a catheter having a catheter shaft 16 emanating from a main catheter or deployment sheath shown at 18 which may have a radiopaque marker 19 at its distal end. Each spine carries a distal ablation electrode 20 which may be bead-or ring-shaped, optionally with a partially flattened or flattened inner side 21 if designed to reduce stowed diameter. Each electrode is possibly 4-5 mm in length and 7-8 French in diameter.

Spaced proximally from each ablation electrode 20 is a bipolar recording electrode, nominally about 2 mm to 5 mm in length, shown at 22. A deflecting or folding, resilient, spine connecting member of non-conducting surface 24 is connected between the distal tips of the V and at maximum expansion of the catheter system is substantially linear. The member 24 is normally a flexible wire and may be of a memoried material such as nitinol® or a spring material and is centrally connected with a non-conducting control element or wire 26 at 27, the axially adjustment of which (indicated at 28 in FIG. 2) controls the expansion/collapse of the catheter system. In the collapsed or folded position shown in FIG. 3, the catheter can be withdrawn back into the sheath.

The expansion of the V controls the relative separation of the electrodes and also the allowable pressure that may be placed on opposing surfaces of a chamber of interest by the electrode during recording and ablation. The expansion of the V also enables the entire system to be moved linearly in a direction substantially parallel to the axis of the sheath 18 inasmuch as the catheter 10 cannot be withdrawn into the sheath while expanded. Retraction or extension of the control member or pull wire 26 causes the wire 24 to deflect or fold thereby collapsing the catheter system which can then be withdrawn into the lumen of the catheter or sheath tube 18.

The sheath or catheter used to house the working catheter associated with the invention may be any type deflectable sheath suitable for vascular navigation with or without a guidewire system and such systems are considered well known. Of course, a variety of working catheters can be sequentially employed while the outer catheter or sheath is in place. Once one is withdrawn, another, possibly different, model may conveniently be substituted and used. Examples of steerable or deflectable sheath can be seen, for example, in copending application Ser. No. 08/148,598, filed Nov. 8, 1993, which is itself a continuation-in-part of Ser. No. 07/976,784, filed Nov. 16, 1992. Both of these applications have common inventorship with the present application.

Figure 6:
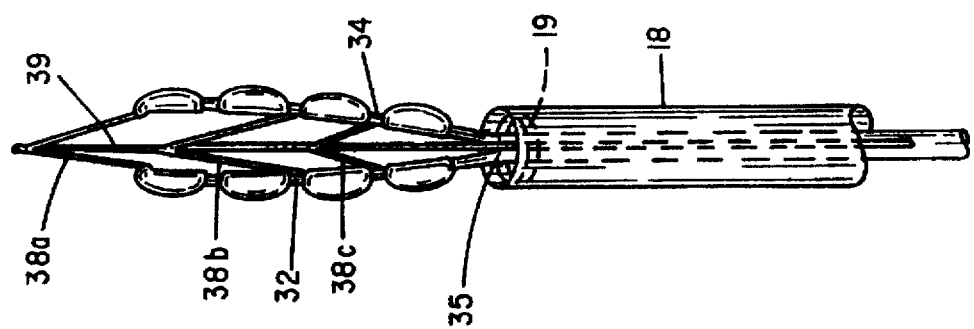
FIGS. 4-6 depict expanded, partially expanded and collapsed or folded views of a catheter having additional ablation electrodes.
Figure 5:
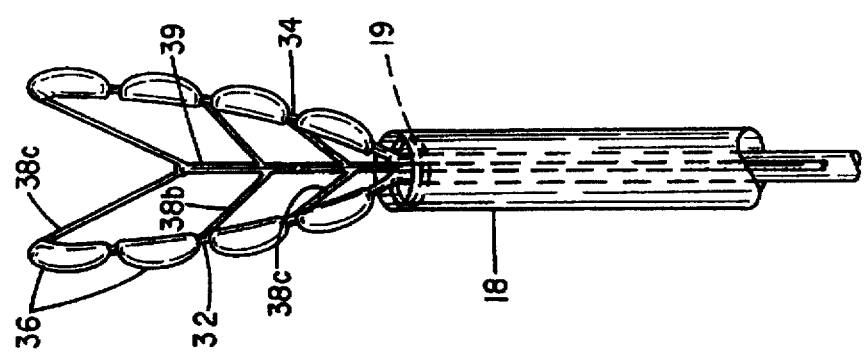
Figure 4:
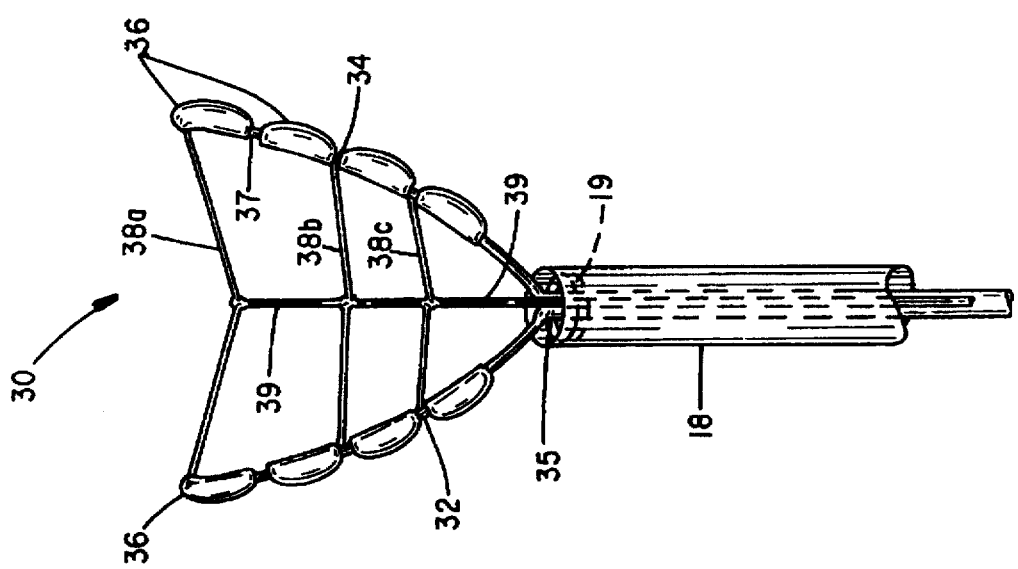

In a second embodiment of the working catheter of the invention, multiple ablation electrodes are distributed along a pair of dual spine members as shown in FIGS. 4–6. These Figures, like FIGS. 1–3, depict the system in various states of expansion or deployment from fully open (FIG. 4) to fully collapsed (FIG. 6). The system of FIGS. 4–6 is deployable in the same manner as that of FIGS. 1–3 from sheath 18. Two spines 32 and 34 with shaft 35 define a basic V or wishbone shape for the working catheter generally at 30. A series of spaced ring-or bead-shaped ablation electrodes 36, with facing surfaces shown in the optional, flattened configuration at 37, are serially deployed along each of the spines. A plurality of memoried or resilient connecting elements 38a, 38b and 38c are attached in substantially spaced parallel relation spanning the two spines 32 and 34 at spaced intervals. The cross-members intersect and are connected intermediately by a common non-conducting control member or wire 39 designed to move axially to expand and collapse the catheter system 30. As noted in FIGS. 5 and 6, the system may be collapsed by axially displacement of the control wire 39 by either retracting the wire in a direction back into the sheath 18 (FIG. 5) or distally away from the sheath 18 as shown in FIG. 6.

While the embodiments illustrated in FIGS. 1–6 depict a pair of spines of substantially common origin, it will be appreciated that any convenient number may be employed if desired. Also, unequal numbers of electrodes may be used on diverse spines or another asymmetric arrangement used. For example, in FIG. 7, a four-spine system is illustrated in which intersecting connected pairs of spines 40 and 40a, and 41 and 41a, are shown. Each pair is further connected by cross members or spaced connecting elements as at 42a–42c and 43a–43c, respectively, all of which are connected to a common control element 44. A common origin is shown at 45 and a directional radiopaque marker at 46.

Figure 10:
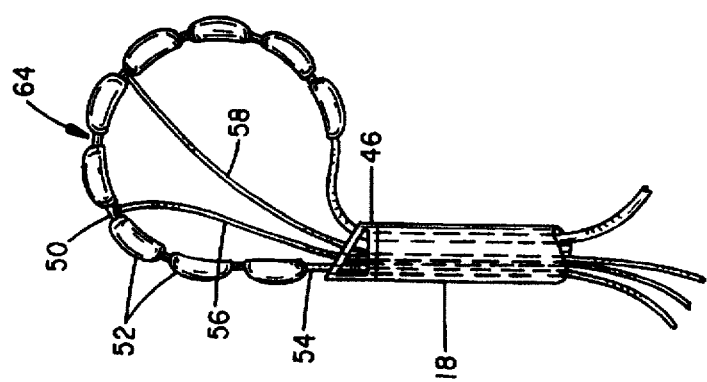
FIGS. 8-10, depict an embodiment of the invention having a single spine member with multiple control elements.
Figure 9:
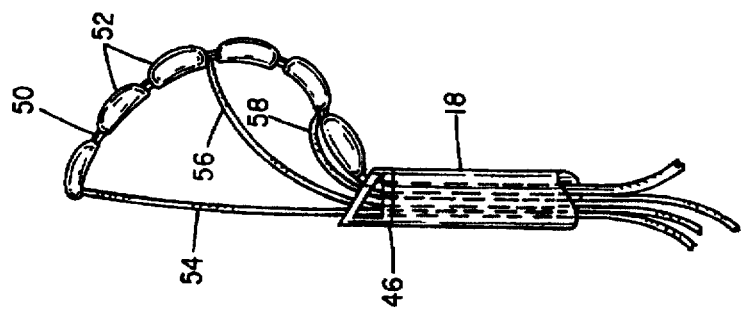
Figure 8:
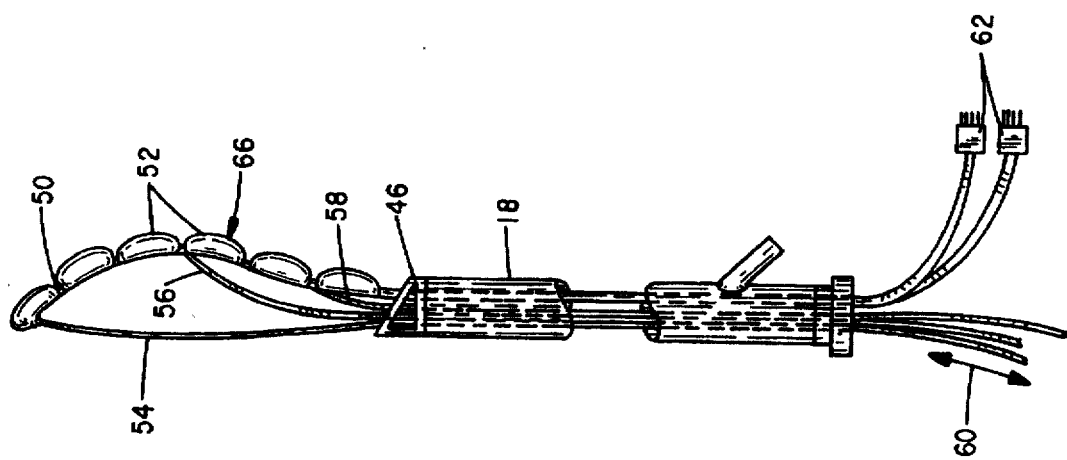

FIGS. 8–10 depict another important embodiment in which a resilient, generally memoried, single spine system or catheter 50 carrying a plurality of mapping/ablating electrodes 52 is provided with a plurality of control elements as at 54, 56 and 58 connected at spaced locations along the spine and axially controllable in any well-known manner from beyond the proximal end of the sheath or catheter 18 as at 60. Proximal, external electrode connections are shown at 62.

Figure 7:
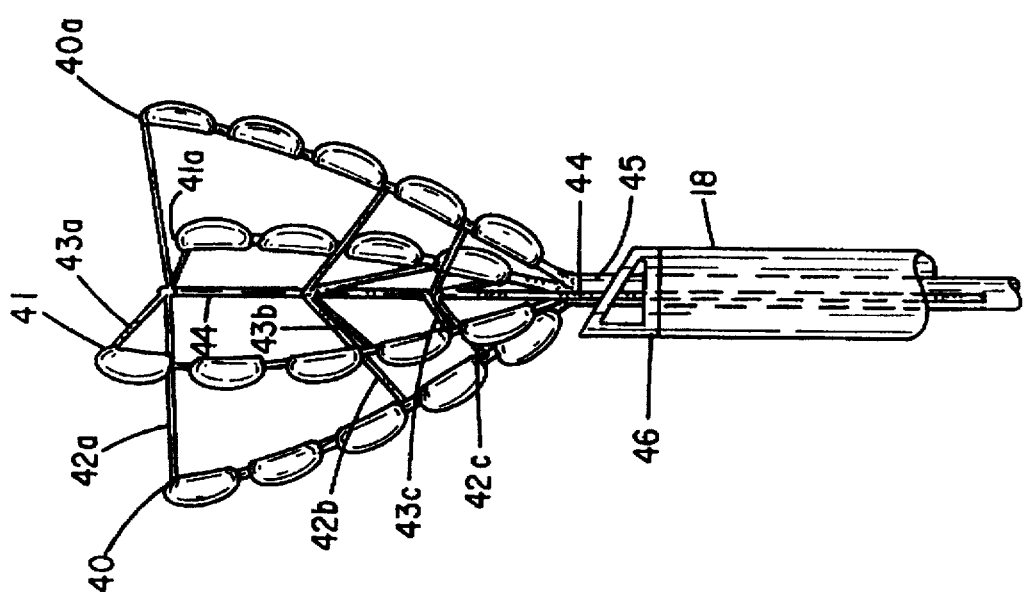
FIG. 7 depicts an alternate embodiment having four spine members.

As shown in the Figures, relative proximal movement of the element 54 can be used to form the spine into a loop as at 64 (FIG. 9) and relative distal displacement of the element 54 and produce a relatively gentle curve at 66 (FIG. 7). Of course, anything therebetween and distortions thereof are also possible. The spine 50 may be memoried to assume any desired shape when deployed in the relaxed state which can be modified upon deployment. Generally, however, the spine is preferably predisposed to straighten. Also, the control elements 54, 56, 58 can have any degree of flexibility (rigidity) desired as well as any tensile. This embodiment offers a great deal of shape and lesion length control.

It will be appreciated that any embodiment of the expanding catheter of the invention can be made any desired size and configured to produce any desired outward force against chamber walls. For example, the number and strength of the connecting elements may be varied. If a weaker or smaller system is not properly sustainable in position in a heart chamber, a larger or possibly stronger model may be readily substituted via the outer catheter or sheath.

In addition, the shafts 16, 35 or outer catheter or sheath may be directionally adjustable to aid in positioning the electrodes as desired. The shafts 16, 35 can also be of a non-linear predisposed, memoried shape that is resumed upon deployment of the working catheter.

Each electrode is separately connected and each spine carries the corresponding number of connecting conductors internally in a lumen or imbedded in the spine, the electrodes having the ability to be energized in any pattern or connected for receiving (recording) as desired. This allows complete operating flexibility in both recording and ablation.

This invention has been described herein in considerable detail to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. An expandable electroded system for recording and ablation designed to traverse a lumen of an elongated outer catheter or sheath and expand upon emergence from an opening in the distal end thereof comprising a pair of proximally constrained diverging spines, said spines being sufficiently rigid to maintain a predisposed shape but adapted to be deflected by the walls of a chamber in which they are deployed, having distal tips free to separate as independent elements, the spines separating to form the shape of a "V" upon expansion and at least one ablation electrode, located on the distal tip of each spine, said system further comprising at least one resilient spine connecting member joining said pair of spines stabilizing and limiting the separation thereof.

2. The apparatus of claim 1 further comprising axially displaceable control element attached to said at least one resilient spine connecting member intermediate said spines and operable axially relative thereto to deflect or release said spine connecting member for causing said spine connecting member to fold or to extend to thereby collapse and expand said electroded system.

3. The apparatus of claim 2 comprising a plurality of said spine connecting members each connected to said control element.

4. The apparatus of claim 2 wherein said expandable system further comprises a plurality of intersecting pairs of diverging spines.

5. The apparatus of claim 4 comprising a plurality of spine connecting members associated with each pair of diverging spines.

6. The apparatus of claim 2 further comprising a plurality of serially spaced ablation electrodes carried by each spine.

7. The apparatus of claim 3 further comprising a plurality of serially spaced ablation electrodes carried by each spine.

8. The apparatus of claim 5 further comprising a plurality of serially spaced ablation electrodes carried by each spine.

9. The apparatus of claim 1 wherein said electrodes are ring or bead electrodes having a length of 3–5 mm.

10. The apparatus of claim 1 further comprising a pair of recording ring electrodes, one fixed to each of said spines proximally spaced from each ablation electrode.

11. The apparatus of claim 6 wherein said electrodes are ring or bead electrodes having a length of 3–5 mm.

12. The apparatus of claim 7 wherein said electrodes are ring or bead electrodes having a length of 3–5 mm.

13. An expanding recording and ablation catheter system comprising:
   (a) an outer catheter or sheath having a lumen therein disposed to carry an inner catheter;
   (b) an inner catheter having a distal end carrying an expanding electroded system;
   (c) an expanding electroded system comprising a pair of elongated spines having proximal and distal ends, said spines being sufficiently rigid to maintain a predisposed shape but adapted to be deflected by the walls of a lumen or cavity of a body organ in which they are deployed, said proximal ends being mutually constrained, and said distal end being free to separate as independent elements and one or more electrodes on each said spines;
   (d) at least one connecting member connected between said pair of spines to control the relative separation thereof; and
   (e) axially displaceable control element connected to said at least one connecting member intermediate said spines for deflecting said at least one connecting member to collapse or deploy the system and to control the separation of said spines.

14. An expanding recording/ablation electrode system designed to be carried in a lumen of an outer sheath or catheter and deployed from a distal port in said outer sheath or catheter in a heart chamber, or other body organ, said recording/ablation system further comprising:
   (a) an outer catheter or sheath having a lumen therein designed to carry an expanding electroded system;
   (b) an elongated inner catheter suitable for insertion through said outer catheter or sheath having a proximal and a distal portion;
   (c) an expanding flexible recording/ablation electroded system having the distal portion of said inner catheter and having a pair of divergent electroded spines each having constrained proximal ends and diverging distal ends said spines being sufficiently rigid to maintain a predisposed shape but adapted to be deflected by the walls of a chamber in which they are deployed;
   (d) control system for controlling the relative separation of said pair of divergent electroded spines between a collapsed, substantially parallel configuration and a fully deployed spread condition; and
   (e) wherein said control system further comprises:
      (1) at least one resilient spine connecting member joining said pair of spines, and
      (2) axially displaceable control element attached to said at least one resilient spine connecting member intermediate said pair of spines and operable axially relative thereto to deflect or release said at least one spine connecting member cause said spine connecting member to fold or to release said resilient spine connecting member to thereby collapse and expand said expandable catheter.

15. The apparatus of claim 14 wherein said distal control element is less flexible than other control elements.

16. A recording/ablation device comprising an electroded spine member designed to be carried by an inner catheter in a lumen of an outer sheath or catheter and to be axially deployed from a distal port in said outer sheath or catheter, said device comprising:
   (a) a flexible element or spine carrying a plurality of serially situated separately connected electrodes;
   (b) a plurality of axially operable control elements having distal ends connected at spaced locations to said flexible element and proximal ends threaded through said catheter or sheath to be controlled beyond said catheter or sheath; and
   (c) wherein the axial adjustment of said control elements adjusts the shape assumed by said flexible element.

17. The apparatus of claim 16 wherein one of said control elements is a distal control element connected in the vicinity of the distal end of said spine.

18. The apparatus of claim 16 wherein said spine is free to rotate relative to the connections between said control element and said spine.

19. An expanding recording and ablation catheter system comprising:
   (a) an outer catheter or sheath having a lumen therein disposed to carry an inner catheter;
   (b) an inner catheter having a distal end carrying an expanding electroded system, said electroded system further comprising:
      (1) a flexible element or spine carrying a plurality of serially situated separately connected electrodes;
      (2) a plurality of axially operable control elements having distal ends connected at spaced locations to said flexible element and proximal ends threaded through said catheter or sheath to be controlled beyond said catheter or sheath; and
      (3) wherein the axial adjustment of said control elements adjusts the shape assumed by said flexible element; and
      (4) wherein one of said control elements is a distal control element connected in the vicinity of the distal end of said spine.

20. The apparatus of claim 19 wherein sufficient axial retraction of said distal control element causes said spine to form a loop.

21. The apparatus of claim 20 wherein the further axial retraction or extension of other control elements distorts said loop.

22. An expanding recording/ablation system designed to be carried in a lumen of a sheath or catheter and deployed from a distal port in said sheath or catheter for use in a heart chamber, or a lumen of a cavity of another body organ, said recording/ablation system comprising:
   (a) an elongated body designed to traverse the lumen of a catheter sheath and having a distal portion comprising an expanding flexible recording/ablation electroded system further comprising one or more pairs of electroded spines said spines being sufficiently rigid to maintain a predisposed shape but adapted to be deflected by the walls of a chamber in which they are deployed, each having constrained proximal ends and separable distal ends;
   (b) spine connecting means comprising a resilient spine connecting member connected between each of said at least one pair of said electroded spines for controlling the separation thereof; and
   (c) an axially displaceable control element attached to each said resilient spine connecting member intermediate the pair of spines connected by said spine connecting member and operable axially relative thereto to cause said spine connecting member to deflect and fold or to be released to thereby collapse and expand said recording/ablation system for controlling the relative separation of each pair of said plurality of electroded spines between a collapsed, substantially parallel configuration and a fully deployed diverging condition.

23. The apparatus of claim 22 comprising a plurality of said spine connecting members each connected to said control element.

24. The apparatus of claim 23 further comprising a plurality of serially spaced ablation electrodes carried by each spine.

25. The apparatus of claim 24 wherein said electrodes are ring or bead electrodes having a length of 3–5 mm.

26. An expanding recording/ablation system designed to be carried in a lumen of a sheath or catheter and deployed from a distal port in said outer sheath or catheter in a heart chamber, or other body organ, said recording/ablation system comprising:

(a) an elongated body designed to traverse the lumen of a catheter or sheath and having a distal portion comprising an expanding flexible recording/ablation electroded system further comprising a plurality of electroded spines each having constrained proximal ends and separable distal ends, said electroded spines further comprising a plurality of serially spaced ablation electrodes carried by each spine;

(b) spine connecting means interconnecting the separable distal ends for controlled separation; and (c) control system for controlling the relative separation of said plurality of electroded spines between a collapsed, substantially parallel configuration and a fully deployed spread condition.

* * * * *